United States Patent
Suchsland et al.

(10) Patent No.: US 6,184,414 B1
(45) Date of Patent: Feb. 6, 2001

(54) PROCESS FOR PRODUCING AMMONIUM-2-HYDROXY-4-(METHYLTHIO)-BUTYRATE, MIXTURES CONTAINING THE SAME IN LIQUID FORM AND THEIR USE

(75) Inventors: Helmut Suchsland; Heinz Kohl, both of Rodenbach (DE)

(73) Assignee: Degussa Aktiengesellschaft, Frankfurt (DE)

( * ) Notice: Under 35 U.S.C. 154(b), the term of this patent shall be extended for 0 days.

(21) Appl. No.: 08/781,833

(22) PCT Filed: Jul. 5, 1995

(86) PCT No.: PCT/EP95/02600

§ 371 Date: Jan. 10, 1997

§ 102(e) Date: Jan. 10, 1997

(87) PCT Pub. No.: WO96/01808

PCT Pub. Date: Jan. 25, 1996

(30) Foreign Application Priority Data

Jul. 11, 1994 (DE) ................................................ 44 24 043

(51) Int. Cl.⁷ ......................... C07C 315/00; C07C 315/06
(52) U.S. Cl. ......................... 562/581; 564/123; 564/125; 564/129; 514/557
(58) Field of Search ........................... 562/581; 514/557; 564/123, 125, 129

(56) References Cited

U.S. PATENT DOCUMENTS 2,745,745  5/1956  Blake et al. ........................ 562/581
4,524,077 * 6/1985  Ruest .................................. 514/557

FOREIGN PATENT DOCUMENTS 915 193  1/1963  (GB) .

OTHER PUBLICATIONS

Lewis, R. Ed Hawley's Condensed Chemical Dictionary, twelfth edition, Jan. 1993. Van Nostrand Reinhold Company, New York. p 890–891.*
Roger G. Bates, "Determination of pH—Theory and Practice", 1973, pp. 15–17, 2nd Ed.

* cited by examiner

Primary Examiner—Frank C. Eisenschenk
Assistant Examiner—Mary K Zeman
(74) Attorney, Agent, or Firm—Pillsbury Madison & Sutro LLP

(57) ABSTRACT

Process for producing ammonium-2-hydroxy-4-(methylthio)-butyrate, mixtures containing the same in liquid form and their use. In order to produce ammonium-2-hydroxy-4-methylthio-n-butyrate and mixtures containing the same with a remarkable fluidity and a very low oligomer proportion by a process based on exclusively "liquid" steps, the reaction mixture is treated with a water-immiscible or partially water-miscible inert solvent, until a first organic extract and a first aqueous raffinate are obtained, and the first organic extract is decomposed into a second organic extract and a second aqueous raffinate by treating it with ammonia and phase separation. Re-extraction of MHA as MHAAS is carried out in the second aqueous raffinate, causing salt formation, and MHAAS is isolated from the second aqueous raffinate. This compound is useful as feedstuff supplement and as methionine substitute.

16 Claims, 5 Drawing Sheets

PROCESS FOR PRODUCING AMMONIUM-2-HYDROXY-4-(METHYLTHIO)-BUTYRATE, MIXTURES CONTAINING THE SAME IN LIQUID FORM AND THEIR USE

This application is based on DE Patent application 4424043.0 filed Jul. 11, 1994 and PCT/EP95/02600 filed Jul. 5, 1995 the contents of which are incorporated hereinto by reference.

The present invention is relative to a novel active substance valuable in animal nutrition and to mixtures containing the same in liquid form as well as to a process of their production. The invention concerns in particular a process of producing ammonium-2-hydroxy-4-methylthio-butyrate (MHAAS) by treating 2-hydroxy-4-methylthio-butyric acid (MHA) with ammonia, which MHA contains both monomers and dimers and higher oligomers and is isolated from a reaction mixture obtained by the attachment of hydrogen cyanide (HCN) to methylmercaptopropionaldehyde (MMP) and by mineral-acidic hydrolysis of the methylmercaptopropionaldehyde cyanohydrin (MMP-CH) obtained thereby.

BACKGROUND OF THE INVENTION

Nourishment-improving feedstuff additives are an indispensable component of animal nutrition today. They serve for a better utilization of the food offered, stimulate growth and promote protein formation. One of the most important of these additives is the essential amino acid methionine, which is quite important as adjuvant especially in the raising of poultry. However, so-called methionine substitutes are becoming increasingly significant in this area since they have growth-stimulating properties similar to those of amino acids known for such properties.

Among these substitutes 2-hydroxy-4-(methylthio)-butyric acid is known as methionine-hydroxy analogue, abbreviated MHA, in racemic form as additive and has become economically significant.

MHA is obtained and used in the form of aqueous solutions with active-substance contents between approximately 88–90%. However, these concentrates contain not only the monomeric acid but also, as a consequence of inner-molecular esterification, oligomers, primarily linear and cyclic dimers as well as, to a lesser extent, tri- and tetramers. It is desirable on account of the known, lower nutritive efficiency of action and the poorer rheological behavior to keep the oligomer content as low as possible. On the other hand, the formation of oligomers is subject, as are all α-hydroxy acids, to the laws of chemical equilibrium and their amount can therefore not be freely selected. Rather, it is a function of the parameters such as concentration, temperature, pH and water content which determine the adjustment of the equilibrium. It is possible to obtain products with a distinctly lower oligomer portion than corresponds to the equilibrium due to the inertia of the equilibration reaction under suitable conditions; the ratio of monomers to the sum of the oligomers is then usually above 4:1 and can even reach values above 5:1. However, the ratio constantly shifts after a fairly long storage in favor of the oligomers until finally, after the adjustment of equilibrium has been completed, the monomer portion has dropped to approximately 2.5 to approximately 3:1 as a function of the water content, temperature and pH. The product "ages".

This ageing process also constitutes an application-specific disadvantage of commercial MHA.

Another production-specific disadvantage is the compulsory accumulation of inorganic ammonium salts associated with the obtention of MHA. Thus, in the production process customary today in the art approximately the same amount of ammonium sulfates are produced per kg MHA as wastewater ballast (see below). However, their removal or workup for being utilized elsewhere is associated with additional expense which makes the process and therewith the target product considerably more expensive.

The methionine substitutes also include certain salt-like compounds of MHA such as, in particular, its calcium salt and mixed calcium ammonium salt. However, they have not achieved the same commercial significance as the free acid, since their production is associated with higher production costs. In addition, they can not be added as simply and homogeneously as powdery, slightly hygroscopic solids into the feedstuff mixtures as the readily sprayable, aqueous concentrates of the free acid.

A further additive of this substance class is ammonium-2-hydroxy-4-(methylthio)-n-butyrate, abbreviated MHAAS. Although it has been known for a rather long time, MHAAS has not been accepted as yet in animal nutrition. This is probably connected in particular with the fact that the salt in its pure form can be isolated only with difficulty and with considerable expense and is obtained either as a viscous oil or as a deliquescent and hygroscopic mass. Also, the handling of such a substance which tends toward inhomogeneity poses problems in the area of application technology, for which reason it is difficult to exactly determine its biological merit. In any case, there has as yet been no secure knowledge about its nutritive equivalence in relation to current market products.

2-hydroxy-4-(methylthio)-n-butyramide, abbreviated MHA amide, is also known as a methionine substitute. However, the purposeful production of the compound, which occurs as intermediate stage in the MHA process, and the separation from the hydrolysis mixtures turn out to be very difficult. Low yields of crystalline MHA amide as well as its nutritive efficiency, which is less compared to that of MHA itself, are also reasons why this substance has remained insignificant commercially.

The general process for producing MHA and its alkaline/alkaline-earth salts starts with 3-methylmercaptoproprionaldehyde, also designated as MMP, which is nitrilized with hydrogen cyanide to 2-hydroxy-4-methylthio-butyronitrile, also designated as MMP-cyanohydrin or MMP-CH (equation I).

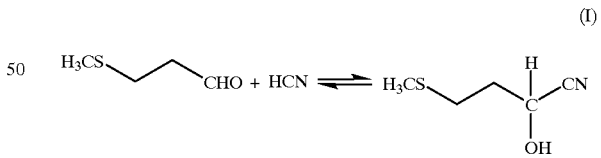

The MMP-cyanohydrin produced is then hydrolyzed customarily with strong mineral acids such as $H_2SO_4$ or HCl via the intermediate stage of 2-hydroxy-4-methylthiobutyramide, also designated as MHA, (equation II),

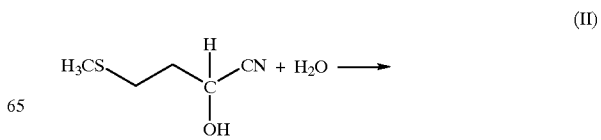

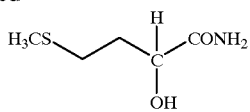

to the methionine hydroxy analogue (MHA) (equation III).

(III)

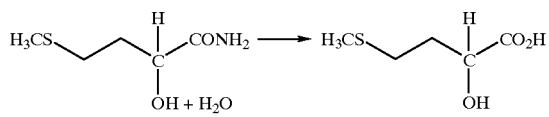

This hydrolysis can be carried out in one stage or in two. In order to arrive at the MHA salt the MHA present in the product mixture is treated in a suitable manner either directly or after previous isolation.

Such different separating techniques as solvent extraction, salting out, precipitation, filtration and concentration can be used for the isolation either individually or in combination.

The MHA acid present can be further processed to the desired MHA salt e.g. by being treated with metal oxides, -hydroxides, -carbonates. In order to arrive at the ammonium salt (MHAAS) MHA can be treated e.g. with ammonia (equation IV):

(IV)

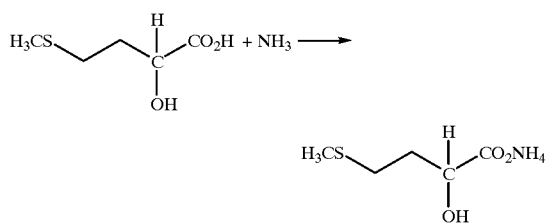

In any case, an important problem is to separate the particular target product from the inorganic accompanying substances and ballast substances, whose workup along with their utilization and removal presents a significant problem according to today's standards and can decisively influence the economy of the basic production process.

A great number of processes are described in the patent literature which have as their subject matter the obtention of MHA as such and also that of the alkaline/alkaline-earth salts, preferably of calcium- and mixed calcium ammonium salts.

The processes of European patents EP 142,488; 143,100; 330,521 and those of American publications U.S. Pat. Nos. 3,773,927 and 4,353,924 concern the production of MHA in the form of aqueous concentrates.

A two-stage hydrolysis starting from MMP-CH forms the basis of the processes of EP patent 142,488 (with sulfuric acid) and of EP patent 143,100 (with mineral acid). Cyanohydrine is hydrated therein at first at relatively low teperatures with e.g. 50–70% sulfuric acid to MHA amide, whereafter the hydrolysis is completed at higher temperatures after dilution with water. Then the reaction mixture is decomposed by extraction, making use of certain solvents partially mixcible with water. MHA is then obtained from the organic extract in cncentrated, aqueous solution by evaporating the solvent under determined conditions in the presence of water. In this manner a high-quality end product is obtained at first in very good yield which is distinguished in particular by little discoloration and a relatively low oligomer portion which is clearly below that of the equilibrium composition. A disadvantage of this process is the problematic nature of the ammonium bisulfate separated in the aqueous raffinate as coupled product, about whose whereabouts and/or removal no data is presented and which results if untreated in a considerable waste-water pollution load which can hardly be justified. The previously mentioned ageing tendency of the monomer/oligomer concentrates obtained which are comparatively low in the fresh state but in any case below the equilibrium ratio is also a disadvantage in this process.

MHA concentrates without the aid of a solvent are obtained according to U.S. Pat. No. 3,773,927 by a two-stage hydrolysis of MMP-CH with hydrochloric acid, subsequent concentration of the reaction mixture along with separation of the crystallized ammonium chloride. However, the MHA obtained in this manner is heavily discolored and rich in oligomers. The ammonium salt isolated as coproduct is also contaminated, so that it has no chance of being utilized and is therefore to be regarded as a worthless ballast substance.

An improvement of the previously cited process is achieved in U.S. Pat. No. 4,353,924 in that the excess mineral acid is neutralized with ammonia or other alkalinely reacting substances. This yields MHA solutions with lower corrosive properties. However, the salt problem remains.

Finally, EP patent 330,521 describes a one-stage hydrolysis process with sulfuric acid which makes do without solvent and in which crystalline ammonium sulfate is obtained as coproduct along with liquid MHA. This goal is achieved in that the reacted saponification mixture is partially neutralized with ammonia so that the ammonium bisulfate produced as well as any free sulfuric acid still present are converted into the neutral ammonium sulfate. Two liquid phases are produced thereby which, for their part, are separated and concentrated by evaporation in order to obtain on the one hand liquid MHA and on the other hand crystalline ammonium sulfate. A suitable combination of the various filtration- and return steps brings it about that no product is lost and the formation of a waste water loaded with salts is avoided. The resulting MHA is of a very good quality. However, in spite of these advantages the process also has significant disadvantages. For the one, the isolated ammonium sulfate has a sticky consistency and is encumbered with an intensive odor, so that the salt must still be purified subsequently e.g. by recrystallization in order to obtain it in saleable form. For the other, the rather dilute procedure in conjunction with the rather high excess of mineral acid necessary thereby results in additional expenses which are reflected in higher supply numbers and a greater energy requirement e.g. in the various concentrating operations. In addition, there is an expensive handling of solids. All these factors render the process considerably more expensive. For the rest, the resulting monomer/oligomer concentrate is subject to the same ageing process as the one obtained according to EP patents 142,488 and 143,100.

The processes of U.S. Pat. Nos. 2,745,745; 2,938,053; 3,175,000; 4,310,690 and GB patents 722,024 and 915,193 are relative to the production of the alkaline/alkaline-earth salts of MHA, especially of the calcium- and mixed calcium ammonium salt. All instances of salt formation in them are preceded by the obtention of the MHA intermediate by mineral-acidic nitrile hydrolysis.

The two-stage hydrolysis with sulfuric acid forms the basis for the processes of U.S. Pat. Nos. 2,745,745; 2,938, 053 and 3,175,000. In the first two publications cited the rather dilute saponification mixture is treated with e.g. calcium hydroxide or -carbonate in an amount which is at least sufficient for bonding the sulfate ions. Calcium sulfate is precipitated thereby and ammonia released, which for its part reacts with MHA to the ammonium salt MHAAS. The salt can be obtained from the solution by concentration by evaporation in impure form as viscous oil or hygroscopic solid. However, it can also be reacted preferably by the addition of more calcium hydroxide/carbonate to the calcium- or calcium ammonium salt of MHA, which are obtained in solid form after the concentration by evaporation. The same result is obtained if the saponification solution is treated immediately with a sufficient excess of the basic calcium compound. MHA amide is used as initial product in GB patent 722,024. For the rest, the process for obtaining the MHA salts is identical with the process described above.

In order to avoid the compulsory case of the worthless calcium sulfate coproduct, in U.S. Pat. No. 3,175,000 the sulfuric-acid saponification mixture is compounded with more ammonium sulfate until saturation. As a result of the salting-out effect two phases form, during which over 90% of the MHA is separated out in the organic phase. This MHA can be further processed directly to the calcium salt. The residual MHA is separated from the aqueous phase by solvent extraction, preferably ether, and reacted to the calcium salt either separately or after being united with the main fraction under evaporation of the solvent. No data is furnished about the whereabouts of the coproduced ammonium sulfate.

The process of U.S. Pat. No. 4,310,690 describes a solution of the ammonium salt problem. In it the saponification mixture is neutralized with sodium hydroxide solution under defined conditions after the two-stage hydrolysis with hydrochloric acid to the extent that the ammonium chloride formed is completely decomposed into sodium chloride and ammonia. In the subsequent treatment with stoichiometric amounts of caustic lime the MHA calcium salt is obtained as suspension in a practically saturated sodium chloride solution. After the solid/liquid separation a part of the wash filtrate is returned for the preparation of the caustic lime suspension and a sodium chloride solution with little organic ballast is obtained as waste water. No data is presented here either about the use or the whereabouts of the coproduct ammonia.

Finally, GB patent 915,193 describes a continuous process for obtaining the calcium- or ammonium salt of MHA. The process is based on the one-stage saponification of MMP cyanohydrin with strong, dilute, approximately 20% sulfuric acid in excess. The MHA is extracted with higher-boiling ethers from the saponification mixture continuously drawn off after 10 hours residence time, whereupon the MHA calcium salt precipitates in fine, crystalline form by a subsequent treatment of the extract with calcium hydroxide/carbonate suspensions in water and is separated off. If gaseous ammonia is conducted into the ethereal MHA extract for the formation of salt, MHAAS forms, which is separated in oily form. However, the return of the aqueous, acidic raffinate into the hydrolysis stage provided in the process results in an accumulation of ammonium salts and can not be carried out in the manner indicated. Moreover, the long reaction times damage the product.

In view of the state of the art discussed here, the present invention has the problem of indicating a process for producing ammonium-2-hydroxy-4-(methylthio)-n-butyrate (MHAAS) which avoids or at least noticeably diminishes the previously mentioned disadvantages which accompany both the production and the use of known methionine substitutes. The process should also be progressive, particularly from the standpoint of environmental compatibility, which can be achieved especially by avoiding environmentally harmful waste water or the compulsory accumulation of inorganic ammonium salts. A further goal of the invention is to make available a novel active substance suitable for animal nutrition or an active-substance mixture in liquid and stable form containing this active substance, that is, especially with an ageing tendency with is considerably reduced or eliminated over the state of the art.

SUMMARY OF THE INVENTION

A process for producing ammonium-2-hydroxy-4-methylthio-n-butyrate (MHAAS) by treating 2-hydroxy-4-methylthio-butyric acid (MHA) with ammonia, which MHA also contains dimers and higher oligomers and is isolated from a reaction mixture obtained by the attachment of hydrogen cyanide (HCN) to methylmercaptopropionaldehyde (MMP) and by mineral-acidic hydrolysis of the methylmercaptopropionaldehyde cyanohydrin (MMP-CH) obtained thereby. The reaction mixture is treated with an inert solvent non-miscible or only partially miscible with water with obtention of a first organic extract and of a first aqueous raffinate. The first organic extract is decomposed by treatment with ammonia and phase separation into a second organic extract and a second aqueous raffinate occurs. Re-extraction of the MHA as MHAAS into the second aqueous raffinate takes place with the formation of salt. The MHAAS is isolated from the second aqueous raffinate in liquid form, generally including less than 10% dimers and oligomers, with a total MHAAS content (including dimers and oligomers) of 70–90% by weight. The new product is suitable for animal nutrition.

As a result of the fact that the reaction mixture is treated with an inert solvent non-miscible or only partially miscible with water under obtention of a first organic extract and of a first aqueous raffinate, that the first organic extract is decomposed by treatment with ammonia under phase separation into a second organic extract and a second aqueous raffinate, with the re-extraction of the MHA as MHAAS into the second aqueous raffinate taking place under the formation of salt, and that the MHAAS is isolated from the second aqueous raffinate, a novel process for producing MHAAS and active-substance mixtures based on it is made available which is based only on "liquid" process steps and is thus technically advantageous for industrial production. In addition, in a preferred embodiment the generating of a waste water loaded with ammonium salts and the coproduction of inorganic ballast substances such as ammonium chloride and -sulfate or calcium sulfate are avoided and a waste water which basically does not require any more chemical treatment is produced.

Furthermore the use of the process of the invention makes available a novel active substance or a novel active-substance mixture in liquid form for the family of methionine substitutes with improved properties which are distinguished in comparison to traditional products of this type by an improved flowability and by an oligomer content which is significantly reduced to the point of converging toward zero.

In addition, the new active substances are not exposed to any appreciable ageing phenomena on account of their weakly acidic to neutral nature, which phenomena stem in known products from an oligomer portion which is constantly changing and usually rising and which can exert an unfavorable influence on the biological efficiency of action and the flow behavior. The new substances therefore have a nutritive effectiveness in particular which also remains constant for a rather long storage time and stays at a constant level.

An important aspect of the process of the invention is the extracting of the solution obtained during the hydrolysis with an inert solvent non-miscible or partially miscible with water under obtention of a first organic extract with the MHA transferred and dissolved therein along with oligomers as well as possibly any residual MHA amide and the obtention of an aqueous, essentially organic-free, first raffinate in the form of a concentrated to saturated ammonium salt solution.

DETAILED DESCRIPTION OF THE INVENTION

All polar to non-polar solvents non-miscible or only partially miscible with water are suitable for the extraction which display an inert behavior under the extraction conditions as well as under conditions of re-extraction of the following step. The following can be cited: Secondary alcohols, ethers, esters, ketones, aliphatic and aromatic hydrocarbons, which can also be chlorinated. Preferred solvents are ketones of C 5 to C 8, especially methylisobutylketone and ethyl-n-amylketone. The extraction can be carried out in any manner familiar to an expert in the art to the extent that it is assured that the product decomposition takes place practically completely, that is, that the MHA, the oligomer portion as well as any residual MHA amide are transferred to the greatest extent possible into the extracting agent; it can be carried out batch-wise or preferably continuously. The ratio of product to extracting agent is not critical but for reasons of effeciency of action a minimum ratio of 1:1 should not be dropped below and for reasons of economy a ratio of 1:3 should not be exceeded. A ratio of 1:1.5–2.0 is preferred.

Another important aspect of the invention is the treatment of the first organic extract with ammonia. This should take place in such a manner that a splitting of the first organic extract into a second organic extract and a second aqueous raffinate becomes possible. This can take place under separation of the phases; the product sought passes thereby into the aqueous phase. This therefore concerns a quasi second extraction step.

The amount and concentration of the ammonia used are not critical in as far as it is assured that an amount sufficient for the complete formation of salt is present. For reasons of economy and savings of energy rather large excesses are avoided as well as concentrations which are too low. An ammonia which is concentrated from high to very high is preferred. The temperatures to be used in both extraction steps are also not critical in as far as the phase-separation behavior is not adversely affected and a formation of emulsion is avoided. Temperatures of 20–60° C. are preferred. Higher temperatures are generally less favorable since undesired evaporation phenomena then occur as a rule.

In a preferred embodiment the first organic extract is compounded in such a manner and in such an amount thereby with concentrated, preferably 25–90% by weight aqueous ammonia solution that the MHA contained therein is essentially completely neutralized to MHAAS. In the neutralization of the acidic, first organic extract even dimers and oligomeric portions of the MHA are converted to the corresponding ammonium salts. The extract obtained thereby essentially contains the extraction solvent whereas the second raffinate therefore comprises the ammonium salts of MHA and its oligomers converted therein as well as any residual MHA amide. In a further aspect of the invention it is advantageous to heat the second, aqueous raffinate before and/or during the isolation of the product striven for, preferably under reflux. This is favorable for the process of the invention in two ways. For the one, the oligomeric portions as well as any residual MHA amide are extensively split to the desired boundary content under formation of further monomeric MHAAS and for the other, a slight amount of MHA desired within the framework of the composition of the invention can be re-formed by hydrolytic splitting of the MHAAS under the release of ammonia.

The "re-extraction" under simultaneous neutralization of the MHA to MHAAS and of the oligomers to $NH_4$ oligomers by ammonia is made possible by virtue of the fact that the cited salts are practically insoluble in the extraction solvents and that any MHA amide which is still present in a slight amount changes readily into the aqueous phase due to its hydrophilic character.

In a preferred process variant any excess ammonia is evaporated out of the second raffinate, optionally after splitting of oligomers and re-formation of a desired amount of MHA, in conjunction with an optional concentration by water evaporation by means of an adiabatic vacuum evaporation cooling with obtention of the sought-after active-substance solution.

In this step the solution containing the target products can be conditioned so that an active-substance concentrate of the composition in accordance with the invention is obtained. This goal is preferably achieved in that the possibly excess ammonia is stripped off, the solution optionally concentrated by further water evaporation to the desired end concentration, the solution cooled off to temperatures below approximately 60° C. with the cooperation of an adiabatic vacuum evaporation cooling and that the resulting solution is adjusted to the desired pH, if necessary by the addition of ammonia and/or water.

Based on the variability of the process steps forming the active-substance solution, it is possible in accordance with the invention to make available an active-substance solution adapted to the climatic and technically conditioned storage conditions within the limits of the invention. Thus, a concentrate is made available e.g. for rather hot climatic zones which has a somewhat higher amount of free MHA, which however, does not exceed a maximum of 20%, in order to counteract in this manner the possible hydrolysis of the MHAAS at rather high temperatures. Since the nutritive efficiency of action of oligomeric-rich solutions advantageously does not decisively deviate from that of a pure MHAAS solution but is clearly different from solutions rich in MHA and oligomers, such a measure supporting the storage stability has no loss of quality as a consequence.

In a further aspect the invention also improves the hydrolysis of the MMP-CH itself in addition for the obtention of the MHAAS out of the reaction mixture obtained by acidic hydrolysis. This known hydrolysis can basically be carried out with known acids such as sulfuric acid or other mineral acids. However, it turned out to be especially logical and therefore also quite especially preferable within the framework of the invention to use HCl for the hydrolysis of the MMP-CH. The use of HCl makes an improved hydrolysis process available which permits, in comparison to the generically known processes in the state of the art, the obtaining of the MHA intermediate stage in a higher yield, purity, with lesser discoloration and with less formation of byproducts as well as essentially free of (odor-intensive) organic accompanying substances. In an advantageous development of the process of the invention the hydrolysis of MMP-CH is carried out in two stages. A hydrolysis is performed in a first stage with aqueous hydrochloric acid with a concentration of 15–40%, preferably 20–37% and especially preferably 30–36% in a temperature range of 20–70° C., preferably 30–60° C. and especially preferably 35–55° C. as well as with a molar ratio of MMP-CH to HCl of 1:1.0–1.5, preferably of 1:1.05–1.3 and especially preferably of 1:1.1–1.2. This produces essentially MHA amide and the reaction mixture is free of cyanohydrin. The hydrolyzing of the reaction mixture in a second stage is also quite especially advantageous, optionally after a preceding dilution with water, at temperatures of 80–110° C., preferably 90–100° C. and especially preferably 90–95° C., in order to essentially complete the hydrolysis of the MHA amide to MHA; The hydrolyzate is then cooled to at least 60° C., advantageously using an adiabatic vacuum evaporation cooling of the reaction solution in order to remove a slight amount of volatile impurities as well as excess hydrochloric acid.

It is advantageous if both hydrolysis stages of the two-stage hydrolysis are carried out with rather highly concentrated hydrochloric acid since this on the one hand avoids rather large excesses of acid and on the other hand the reaction proceeds under protective conditions. For example, a 37 to at least approximately 30% HCl requires a molar excess of only 5 to a maximum of 15% whereas the associated reaction temperatures and reaction times can be limited to 30–50° C./10–30 minutes in stage (1) and to 90–95° C./45–60 minutes in step (2).

The following adiabatic evaporation cooling serves both for an energy-saving cooling as well as to remove slight, volatile impurities from the reaction mixture which could possibly have been brought into the latter already with the educt (HCN, MMP). Even the removal of a part of the hydrochloric-acid excess can be an advantage. This step can also be eliminated if required.

Furthermore, it is favorable in a preferred process modification to treat the reaction mixture with a base after hydrolysis and before the treatment with solvent.

The base serves to blunt or pre-neutralize the excess free mineral acid, which assures a pH of approximately −1 or even more acidic up to the blunting.

For a description of superacids and negative pH, see "SUPERACIDS" by Olah et al., John Wiley & Sons, particularly pages 7–11 and 24–27.

The solution is preferably blunted with aqueous or preferably gaseous ammonia in order to neutralize the remaining, possible excess hydrochloric acid while adjusting a pH in the range of −0.5 to +0.5, preferably −0.2 to +0.2 with obtention of an aqueous solution containing essentially MHA along with component oligomers as well as ammonium chloride.

The partial neutralization of the reaction mixture with (preferably gaseous) ammonia for blunting the excess mineral acid prevents an accumulation of the latter in the subsequent extractive decomposition of product and therewith, in the final analysis, an accumulation of ammonium salts in the target product.

In a further aspect it is preferred for the invention that the substances occurring in the process are conducted to the extent possible in a circuit, reused or converted into a form which can be removed without danger.

Thus, when hydrochloric acid is used for the hydrolysis the first raffinate, containing essentially ammonium chloride, is advantageously neutralized with sodium hydroxide solution up to pH'es of at least 8 under the release of ammonia and the formation of a sodium chloride solution saturated with ammonia. The distilling off and concentrating of the ammonia contained in various steps of the process in one or more stages is also preferred. On the one hand an aqueous ammonia solution which is highly to very highly concentrated is obtained with and without using pressure and optional rectifying conditions which solution is returned into the treatment of the first organic extract. On the other hand an essentially ammonia-free solution containing common salt is obtained which can be supplied to a biological waste-water treatment. The addressed neutralization with NaOH, in which the ammonia which is required for the MHA conversion to MHAAS and which is formed primarily from the nitrile nitrogen of the educt is recovered, is preferably carried out with concentrated sodium hydroxide solution.

This neutralization treatment can take place either separately or in combination with following distillation steps and concentration steps. In both instances techniques known to an expert in the art and suitable apparatuses are used. This also applies to the accompanying concentration, which can be carried out in one or more steps and as a function of the desired concentration with or without the use of pressure according to methods known in the art.

The solvent phase obtained in the MHA conversion and re-extraction as second organic extract is advantageously subjected partially or entirely to a purification distillation in order to avoid the accumulation of impurities, which can be carried out, depending on the type of solvent used and on the amount of dissolved water, in the form of a strip distillation or under azeotropic and/or rectifying conditions. This step can be eliminated intermittently or even entirely if necessary.

It can be especially advantageous for the invention to carry out the various process steps intermittently or continuously or even combined with each other. Thus, it can be advantageous to perform the reaction steps in batches and the workup steps in a continuous manner. However, a production and workup which are only in batches or only fully continuous are of course also possible. A method of operation which is at least partially continuous makes possible the use of protective process conditions and a lesser product loading.

The fact is also especially advantageous over known processes in the art that the process of the invention contains no measures for suppressing or holding back the oligomers since the oligomers are extensively split in it. A further advantage of the process of the invention is the elimination of a solid treatment since no waste salt is produced and the ammonium nitrogen formed in the hydrolysis remains in the active substance without adversely influencing the properties of the active substance.

Thus, a novel process for this active-substance formulation is made available within the framework of the present invention which process produces no waste water requiring treatment and containing ammonium salt and/or produces no crystalline ammonium salts as coupling products, consists only of liquid process steps and is therefore simple and economical to carry out and which permits the production of the target product in the generically known process part of the hydrolysis under improved production conditions with improved product quality and lesser formation of byproducts and also requires no further auxiliary chemicals for the obtention of the final product with the exception of the sodium hydroxide solution to be used for the product decomposition as well as of the extraction solvent, which auxiliary chemicals would increase the price of the process.

The process described in the individual steps naturally allows a multiplicity of possible forms. However, parameters and conditions should be selected which permit the process to be carried out in a simple and economical manner and which also produce excellent results in yield and product purity.

The manner of production and of isolation also render advantageous the obtention of an approximately 80–90% end product in the form of its ammonium salt with subordinate admixtures of free MHA, possibly along with its amide, with extremely slight discoloration, good flowability, sufficient thermal stability with a predeterminable amount of oligomer which is low to converging toward zero (if desired) and which is preferably approximately 0.1 to 2.0% so that an active-substance combination is produced which is novel in its category, can no longer age in comparison to the known products and therefore does not have the disadvantages and uncertainties associated with handling and storage.

The invention therefore also has as subject matter an ammonium-2-hydroxy-4-methylthio-n-butyrate (MHAAS) in liquid form with a total MHAAS content comprising dimeric and oligomeric components of 70–90% by weight, preferably 80–90% by weight and especially preferably 84–88% by weight.

The MHAAS of the invention is characterized with advantage by an amount of dimers and oligomers of $\leq 10\%$ by weight, preferably $\leq 6\%$ by weight and quite especially preferably 1% by weight relative to the sum MHAAS+dimer+oligomer which amount changes only little in time to not at all.

The invention also includes mixtures of ammonium-2-hydroxy-4-methylthio-n-butyrate (MHAAS) with 2-hydroxy-4-(methylthio)-n-butyric acid (MHA) and/or 2-hydroxy-4-(methylthio)-n-butyramide (MHA amide).

These mixtures preferably have an amount of MHA of up to 20% by weight and/or of MHA amide of up to 5% by weight relative to the sum of MHAAS+MHA+MHA amide.

In a further advantageous embodiment the mixtures are characterized by an amount of dimers and oligomers of MHAAS, MHA and/or MHA amide of $\leq 10$, preferably $\leq 6$ and quite especially preferably $\leq 1\%$ by weight relative to the sum MHAAS+MHA+MHA amide+their dimers and oligomers, which amount changes only little in time or not at all.

Solutions containing MHAAS obtained according to the process of the invention as main component also preferably have a pH in the state which is stable in storage of 3.0 to 7.5, preferably 4.0–7.0 and especially preferably 5.0–6.0. They are further distinguished by extremely slight discoloration, good flowability and satisfactory thermal stability.

Active-substance concentrates containing MHAAS obtainable according to the invention as main component and optionally MHA and/or MHA amide as subordinate secondary components are excellent feedstuff additives with nutrition-improving and growth-promoting qualities.

BRIEF DESCRIPTION OF THE DRAWINGS

The invention is explained further in the following using examples and referring to the attached drawings. The percent data refers to % by weight unless otherwise indicated.

FIG. 4A top shows a recording of the weight increase in (g) of broilers compared to the supplemented methionine equivalents (%) for various methionine sources in order to clarify the influence of various methionine sources on the performance of broilers 7–28 days old.

FIG. 5A top shows a graphic view of the weight increase of broilers in (g) compared to the supplemented methionine equivalents (%) for the various methionine sources in order to clarify the nutritive efficiency of DL-MHA (free acid), DL-MHA (ammonium salt) and DL-methionine.

EXAMPLE 1

Figure 1:
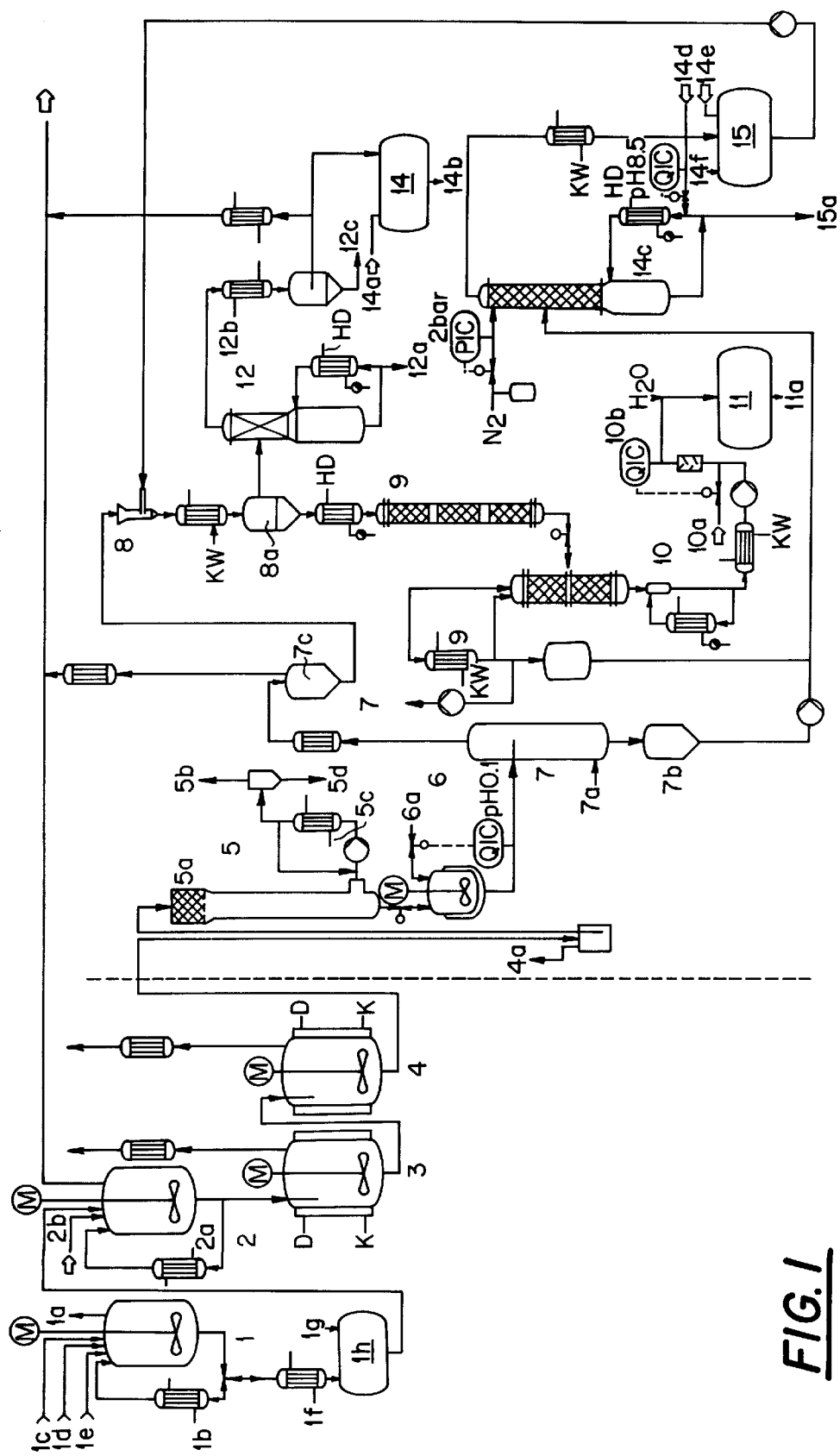
FIG. 1 shows a schematic view of a system for carrying out the process of the invention.

103.6 g 37% hydrochloric acid (1.05 mole) were placed in a reaction vessel equipped with intensive agitator and reflux condenser at 38–40° C. Within 30 minutes 132.5 g 99.0% MMP-CH (1.0 mole) which had been prepared according to known methods was added at this temperature under intensive agitation and cooling. The mixture was allowed to react for 15 minutes while being turbined with the temperatures maintained constant, whereupon the complete conversion of the cyanohydrin was determined by HPLC analysis. Approximately 90% of the educt had been converted to MHA amide and approximately 10% to MHA. The reactor contents were then diluted with 50 g water, heated to 90/91° C. and agitated for 45 minutes. After the completeness of the hydrolysis of the amide stage to the free acid had been checked by HPLC the reaction mixture was cooled down with the aid of a vacuum evaporation cooling to approximately 40° C., during which slight amounts of volatile components and impurities (HCN, among others) were stripped off. The resulting, slightly discolored and almost odorless saponification solution with a pH of around −0.9 was blunted to a pH of +0.1 in order to bind the excess hydrochloric acid with approximately 5% ammonia solution and then extracted with 250 ml methylisobutylketone twice. The combined extracts with a total MHA content of approximately 27%, of which approximately 2.16% were present in oligomeric, primarily dimeric form, were then compounded with 50 g water and shaken out thereafter with 88.5 g 25% ammonia solution (1.3 moles). All MHA species were converted thereby into their ammonia salts (MHAAS, $NH_4$ oligomers), which were eluted just as any residual MHA amide practically completely into the aqueous/ammoniacal phase. The eluate, the separated lower phase, was now heated 35 minutes on the reflux, then evaporated to low bulk under removal of the excess ammonia as well as any solvent residue still present to a concentration of about 85–86 total MHA. 189.8 g solution with 85.0% MHAAS (monomer), 0.44% MHA amide, 0.16% $NH_4$ dimers and 15% water were obtained. The total yield was 97.1% relative to MMP-CH used. The solution was colored pale yellow, odorless, free-flowing and stable in storage for months without changes with a pH of 6.5 at normal temperatures.

The MIBK phase obtained after the re-extraction contained <0.03% of MHAAS and approximately 0.1% of its organic impurities (MHA oligomers). It was subjected to a strip distillation for purification of the solvent. The regenerated MIBK was reserved for following batches after loss supplementation. The bottom product was rejected or removed.

The aqueous phase resulting from the first extraction, which phase consisted essentially of a saturated ammonium chloride solution, the so-called primary raffinate, was transferred into a heated agitating apparatus with infeed funnel, M & R devices for temperature and pH as well as a reflux condenser with a dephlegmator set on it along with a connected absorption receiver cooled down to $-5°$ C. The raffinate was neutralized under constant heating by the addition of concentrated sodium hydroxide solution to a pH of at least 8.5. The ammonia released thereby was absorbed in the receiver loaded with water and recovered in the form of a 20–25% solution and made available therewith for further following batches. An essentially organic-free wastewater solution saturated with sodium chloride was obtained as bottom product which required as such no more treatment and was rejected or removed.

EXAMPLES 2–5

The same process as in example 1 was used; however, instead of MIBK for the extractive decomposition of product successive solvents were used: Methylisopropylketone, ethyl-n-amylketone, methyl-t-butylether and toluene. Similar results were achieved basically using the same workup method and the recovered 20–25% ammonia solutions were used, after appropriate loss supplementation of the preceding batch, for the converting and eluting of the total MHA to its ammonium salts. In the case of toluene an extraction was carried out four times with 250 ml per time; however, a distillative purification of the solvent for a possible following batch was able to be eliminated. In the case of methyl-t-butylether the hydrolysate was cooled off to approximately 20° C. before the extraction.

In all instances brightly colored, odorless and free-flowing solutions with total MHAAS contents of 84–86% were obtained after the conditioning. The amount of $NH_4$ oligomers (dimers) did not exceed 0.2% in any instance and the MHA amide content was able to be limited at below 1.2% (relative to total MHAAS).

EXAMPLE 6

108.5 g 37% hydrochloric acid (1.1 moles) were placed in a reaction apparatus like the one described in example 1 at 30° C. Within 30 minutes 132.5 g 99% MMP-CH (1.0 mole) were added at this temperature under intensive agitation and cooling. After a further 10 minutes of agitation the conversion of the cyanohydrin was complete and could no longer be demonstrated analytically. The reactor contents were then heated in approximately 15 minutes to 90° C. and turbined a further 30 minutes at this temperature. The mixture was then cooled down to approximately 40° C. without the aid of an evaporation cooling. The ammonium chloride which crystallized out thereby was brought back into solution by the addition of 50 water. 302.5 g of a practically colorless solution with a slight but pleasant odor with the following composition were obtained:

43.80% MHA monomer, 5.46% MHA dimer+trimer, 0.17% MHA amide, 17.52% ammonium chloride and 33.05% water. The ratio of monomer to oligomer was 8.03:1 with 11.07% oligomers in the total MHA. the total yield of MHA+oligomers+amide was 99.5% relative to MMP-CH used. The pH was approximately $-1.0$.

The solution was extracted twice with 300 ml MIBK per time. The combined extracts were evaporated to low bulk down to 60% by volume in order to remove the component, dissolved hydrochloric acid during which the main amount was distilled off in the form of a ternary azeotrope. The two-phase vapor condensate caught in a separator was treated with dilute ammonia solution in order to neutralize the hydrochloric acid. After the phase separation the upper phase was combined with the extract concentrate whereas the lower phase was added to the primary raffinate. The combined extracts with a total MHA content of approximately 26% were shaken out with 102 g 20% ammonia solution (1.5 moles), during which the MHA including oligomers and residual amide was eluted practically completely into the aqueous phase, the former as ammonium salts. The eluate was heated 25 minutes to reflux and then evaporated to low bulk under removal of the excess ammonia. 193.5 g of a pale yellow solution was obtained with the following composition:

85.2% MHAAS, 0.69% MHA amide, 0.09% dimers, 14.0% $H_2O$ and 0.1% $Cl^-$. The solution had a pH of 6.8. It had a satisfactory storage stability, was free-flowing and practically odorless.

The primary raffinate was combined with ammonia-containing condensates and treated for ammonia recovery as described in example 1.

EXAMPLE 7

2.2 moles 30% hydrochloric acid were placed in a reaction apparatus. 2.0 moles 97.8% MMP-CH were charged 20 minutes under agitation and cooling while the temperature rose to 45° C. The mixture was agitated under gentle cooling at 45–50° C. a further 30 minutes, whereupon the complete conversion of the cyanohydrin was determined. The mixture was then heated in 20 minutes to 92° C. and the hydrolysis completed within a further 60 minutes at this temperature. The product decomposition and product workup subsequently carried out were performed as described in example 1. After the concluding conditioning 356 g of a concentrate was obtained with the following composition:

Total MHA 80.36 of which 2.76% free MHA, 1.2% MHA amide and 0.16% dimers. Furthermore, the solution contained 8.65% $NH_3$, 10.9% $H_2O$ and 1.34 $Cl^-$; the MHAAS content was 84.87%, the PH was approximately 6.4. The total yield was 95.2 calculated as MHA monomer and relative to MMP-CH used. The solution was unchanged in its composition after 2 months of storage.

The evaporation residue retained in the purification distillation of the MIBK phase was 4.4 g and was insoluble in water.

EXAMPLE 8

134 g 30% hydrochloric acid (1.1 moles) were placed in a reaction vessel according to example 1. 132.5 g 99% MMP-CH (1.0 mole) were added thereto under agitation and cooling within 30 minutes while the temperature was limited to 40° C. The mixture was then agitated 15 minutes further and was free of cyanohydrin thereafter. The mixture was then heated as quickly as possible to 90° C. and hydrolyzed 45 minutes at this temperature. The reaction mixture was cooled down to about 30° C. (without evaporation cooling)

and blunted with 5% ammonia to a pH of +0.1. Two extractions were then carried out with 250 ml MIBK each. The pH of the organic phase was approximately +0.3. After the phase separation the combined extracts were shaken out with 1.5 moles 20% ammonia. The MHA species converted thereby into their ammonium salts, including any residual MHA amide still present as MHAAS and $NH_4$ oligomers, were eluted practically completely into the aqueous phase. The slightly turbid organic phase was washed with 50 ml water, whereupon the latter was obtained as clear solution. The wash water was united with the eluate and the resulting aqueous phase heated 50 minutes on the reflux, during which the oligomers as well as MHA amide were split down to slight residual constituents. After evaporation to low bulk on a rotary evaporator 170 g of a solution colored pale yellow with a pH of 6.0 were obtained with the following composition:

Total MHA 88.0%, of which 81.4% as MHAAS and 6.6% as free MHA, MHA amide 0.5%, <0.2% $NH_4$ dimers, 1.2% $NH_4Cl$, 9.2% $NH_3$ and 9.2% $H_2O$. The total yield was 99.7%, the concentrate had very good storage stability.

Moreover, 220 ml raffinate solution were obtained from the first extraction (primary raffinate) which was a practically saturated ammonium chloride solution and had a ph of +0.15. The latter was neutralized according to the method described in example 1 with 45% sodium hydroxide solution to a pH of 11.8. Approximately 90% of theory of the total nitrogen was recovered thereby in the form of a 20% $NH_3$ solution. The bottom product of 225 g obtained after the decocting of the raffinate was a saturated sodium chloride solution which was essentially organic-free and free of ammonia.

EXAMPLE 9

The procedure described in example 8 was followed; however, 140 g 30% hydrochloric acid (1.15 moles) were used for the saponification of 1.0 mole MMP-CH and the temperature of the first stage was raised to 67° C. and that of the second stage to 93° C. The eluate obtained after the extraction with MIBK as well as re-extraction with 20% ammonia solution (1.5 moles) was protectively dealcoholized in a vacuum. 202 g of a solution with the following composition were obtained thereafter:

MHAAS determined as MHA 59.8%, $NH_4$ dimers+trimers 10.3% and 28.8% $H_2O$. After the following heat treatment (45 minutes under reflux) the dimers were split down to a slight remainder.

EXAMPLE 10

The procedure described in example 8 was followed; however, 1 mole MMP-CH and 200 g 22% hydrochloric acid (1.2 moles) were used for the saponification and the temperature in the first stage raised to 65° C. and that of the second stage to 107° C. In addition, the reaction time in the second stage was extended by 70 minutes. 162 g of a brown-colored concentrate with total MHA of 84.8% was obtained. Of this, 79.0% was present as MHAAS and 5.8% as free MHA. In addition, the solution contained 1.56% $NH_4Cl$. The total yield was 91.5%.

EXAMPLE 11

814.5 g 99% MMP-CH (6.15 moles) were reacted in a coolable and heatable reaction apparatus equipped with infeed funnel, intensive agitator and reflux condenser with 800 g of a 32% hydrochloric acid (7.01 moles 14 molar % excess) in the following manner:

The hydrochloric acid was placed in a receiver under ice-bath cooling. The MMP-CH was then charged in approximately 30 minutes during which the temperature did not rise above 40° C. and the reaction heat of −91 kJ/mole MMP-CH (=−22.0 kcal) was removed via the external cooling. The mixture was then allowed to react another 15 minutes without further cooling, during which the temperature dropped to 45° C. The reactor contents were then heated by a rapid-heating thermal bath to 91° C. and agitated a further 45 minutes at this temperature. The completeness of the conversion was monitored in both stages by HPLC analysis. The thermal bath was then removed and the apparatus connected to a water-jet vacuum. The mixture was cooled down to approximately 60° C. by adiabatic evaporation cooling, during which 55 g $H_2O$ along with 14 g HCl and approximately 4 g organic impurities were stripped off at the same time. After stress relief the hydrolyzate obtained, which had a pH of −0.8, was neutralized by the addition of 15 g 20% ammonia solution to a value of +0.1 (preneutralization). Then, 1545 g of a hardly discolored hydrolyzate solution with the following composition were obtained:

56.5% MHA, 1.8% MHA dimer+trimer, 0.4% MHA amide, 0.6% HCl, 21.4% $NH_4Cl$ and 19.3% $H_2O$.

The solution was transferred into a measuring receiver tempered and heated to approximately 40° C. From there the solution was continuously charged into the upper third of a jacketed packed column brought to the same temperature (80 cm long and 2 cm ø) with upper and lower quiescent zones at a rate of 31 g/min while 1800 g MIBK (2245 ml) were continuously fed into the lower third with the aid of a dosing pump at a rate of 36 g/min. A total of 2717 g extraction solution with the following composition were obtained at the top in a cooled receiver:

66% MIBK, 33.3% total MHA, 0.2% MHA amide as well as 0.2% HCl and 0.4% $H_2O$. The raffinate of about 630 g running off consisted essentially of a supersaturated $NH_4Cl$ solution of around 40% salt content with 0.8% MIBK and traces of MHA. It was fed under dilution to approximately 35% $NH_4Cl$ content to the neutralization apparatus described in example 1 and worked up as described there under recovery of approximately 90% of the ammonia to be expected.

The extraction solution was transferred into a heatable agitator apparatus with reflux condenser and phase-separation vessel connected on the bottom and intensively mixed for approximately 10 minutes after the successive addition of 448 g 25% ammonia. After the agitation was turned off a short calming time of a few minutes was observed. Thereafter, two phases with a sharp interface line had formed. After the phase separation carried out via the connected separator the eluate, the aqueous lower phase, was returned into the agitator container and heated 30 minutes on the reflux. Then a water-jet vacuum was applied and the solution cooled down to 50° C. under evaporation cooling. The excess ammonia of 6.8 g together with approximately 18 g water was stripped off thereby.

Composition of the solution before the reflux treatment:

Total amount 1357 g with 71.58% MHAAS, 2.06% MHA-$NH_4$ dimer+trimer, 0.44% MHA amide, 0.5% $NH_3$, 0.65% $NH_4Cl$, 24.76% $H_2O$.

Composition of the end concentrate after the splitting and concentrating:

Total amount 1182.2 g with 84.71% MHAAS, 0.17% MHA-$NH_4$ dimer+trimer, 0.50% MHA amide, 0.74% $NH_4Cl$, 13.87% $H_2O$.

The total yield, calculated as MHA and relative to MMP-CH used, was 98.4%. The solution had a pale yellow color and a pH of 6.6. It was odorless, free-flowing and stable in storage at 20–40° C.

The MIBK upper phase obtained after the phase separation was distilled out on a rotary evaporator. 99% of the solvent used was recovered. In addition, an evaporation residue of 12 g was obtained which was insoluble in water.

EXAMPLE 12

An eluate with 69.4% MHAAS (monomer), 3.6% MHA-$NH_4$ dimer+trimer, 0.7% MHA amide and 0.7% $NH_4Cl$ was obtained in accordance with the general procedure of example 11 which was worked up in the following manner:

The solution was divided into 4 equal parts and the four aliquots subjected to a heat treatment of different lengths. In test 1 the matter was heated for 45 minutes, in test 2 for 60 minutes, in test 3 for 90 minutes on the reflux. In test 4 gaseous ammonia was bubbled in during the 60 minutes of heating time. It was found that the amount of free MHA rapidly rose with increasing heating time after the concentrating up to a total concentration of 76% MHA corresponding to 84.7% MHAAS with loss of ammonia and lowering of pH while the amount of oligomers dropped to below 0.2% and the MHA amide amount remained constant. There was also a rise of the latter only in test 4 whereas, conversely, the amount of free MHA dropped again. The following was found in detail:

1. With 45 minutes 100° C.: 71.4% MHAAS and 4.6% MHA-free, pH 6.3, stable in storage 40° C.

2. With 60 minutes 100° C.: 66.0% MHAAS and 10.0% MHA-free, pH 5.8, stable in storage 50° C.

3. With 90 minutes 100° C.: 58.0% MHAAS and 18.0% MHA-free, pH 4.9, stable in storage 55° C.

4. With 60 minutes 100° C: 74.0% MHAAS and 2.0% MHA-free, pH 6.5, stable in storage 35° C.+bubbling in of $NH_3$ gas 2.0% MHA amide

EXAMPLE 13

A hydrolyzate was produced as described in example 6 and extracted with two times 300 ml MIBK=481 g. A solution with 24% total MHA was obtained of which 11.1% was present in the form of dimers+trimers. The extract solution was concentrated to a content of 30% total MHA in order to remove the excess hydrochloric acid. The turbidity which occurred thereby was clarified by the addition of 20 ml water, whereupon 1.5 moles gaseous ammonia were introduced at 20° C. This corresponded to an ammonia concentration of 45.5%. The lower phase separating off was allowed to stand several hours at 30° C. and then evaporated to low bulk at 60° C. under a vacuum. A concentrate with a yellowish color and a content of 76.3% total MHA corresponding to 85.2% MHAAS was obtained. The amount of oligomers was degraded to <0.2% whereas the amount of MHA amide had risen to 1.1%. The pH of the solution was approximately 6.5.

EXAMPLE 14

A reaction was carried out as described in example 7 and worked up according to the general procedure indicated in example 1 but with the following changes:

The 27.1% total MHA solution obtained after the MIBK extraction was halved. In test 1 the re-extraction was carried out with 1.1 moles 25% ammonia and in test 2 with 0.9 mole 25% ammonia. The eluates obtained were subsequently heated 30 minutes on the reflux and then anlyzed:

Concentrate composition from test 1
70.4% MHAAS, 6.2% MHA, 0.60% MHA amide, 0.26% MHA-$NH_4$ dimer+trimer.

Concentrate composition from test 2
64.5% MHAAS, 12.1% MHA, 0.45% MHA amide, 0.46% MHA-$NH_4$ dimer+trimer.

Concentrate 1 and a ph of 6.1 and was stable in storage to ≧45° C.

Concentrate 2 had a pH of 5.6 and was stable in storage to 60° C.

EXAMPLE 15

An MHA product solution was produced according to EP 142,488, example 5 with 89.2% total MHA by hydrolysis of the MMP-CH with sulfuric acid and following MIBK extraction along with subsequent water-vapor distillation. The resulting concentrate had a content of 72.7% MHA monomer and 16.5% MHA dimer+trimer. This solution was neutralized with gaseous ammonia to the extent that 78% of the MHA was bound as ammonium salt. After the solution had been heated 45 minutes on the reflux the ratio of MHA monomer to MHA oligomer was rechecked by HPLC analysis. It was found that the oligomer component had receded to 6.0% and the monomer component had been raised to 83.2%.

Figure 2:
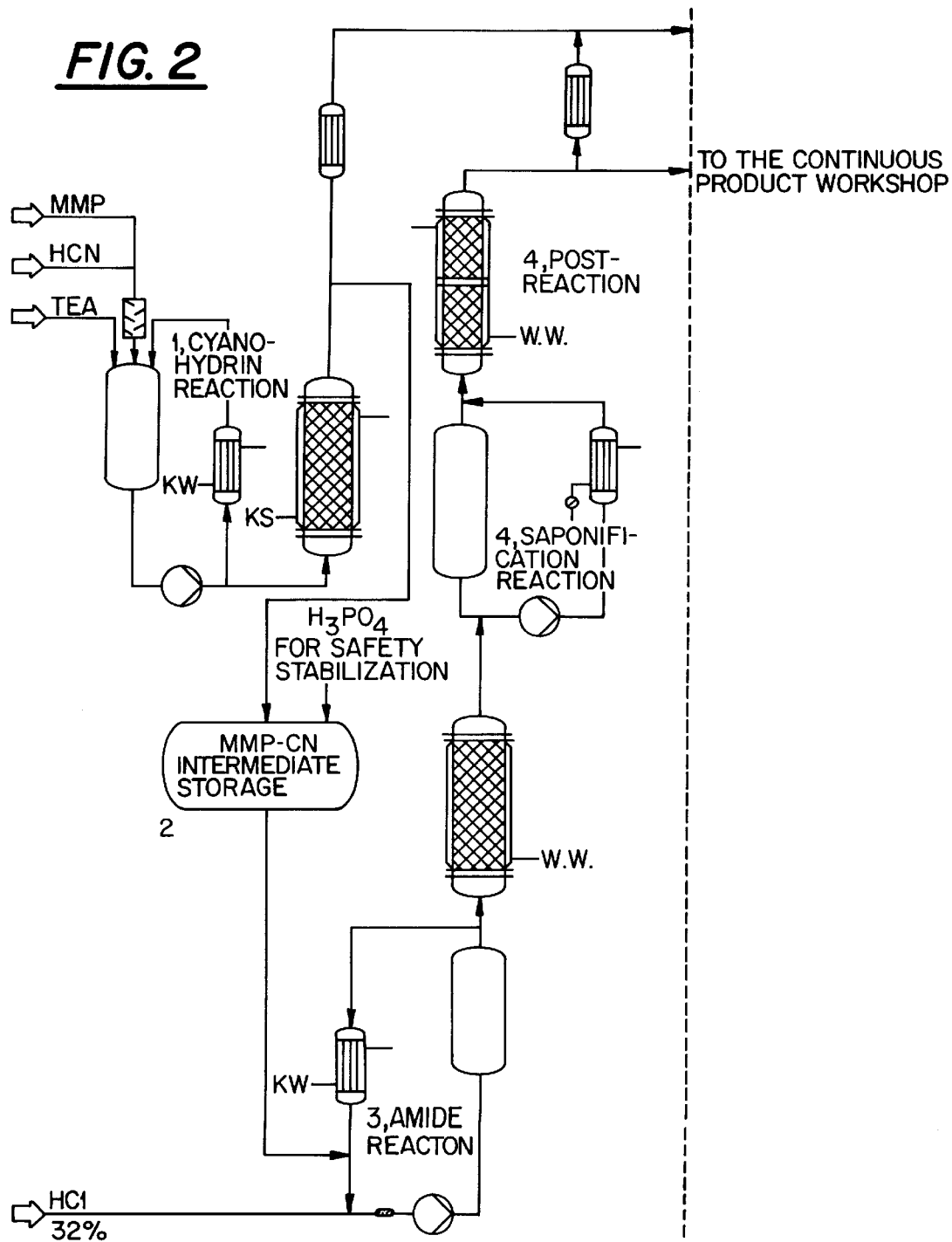
FIG. 2 shows a schematic view of another embodiment of a system for carrying out a modification of the process of the invention.
Figure 3:
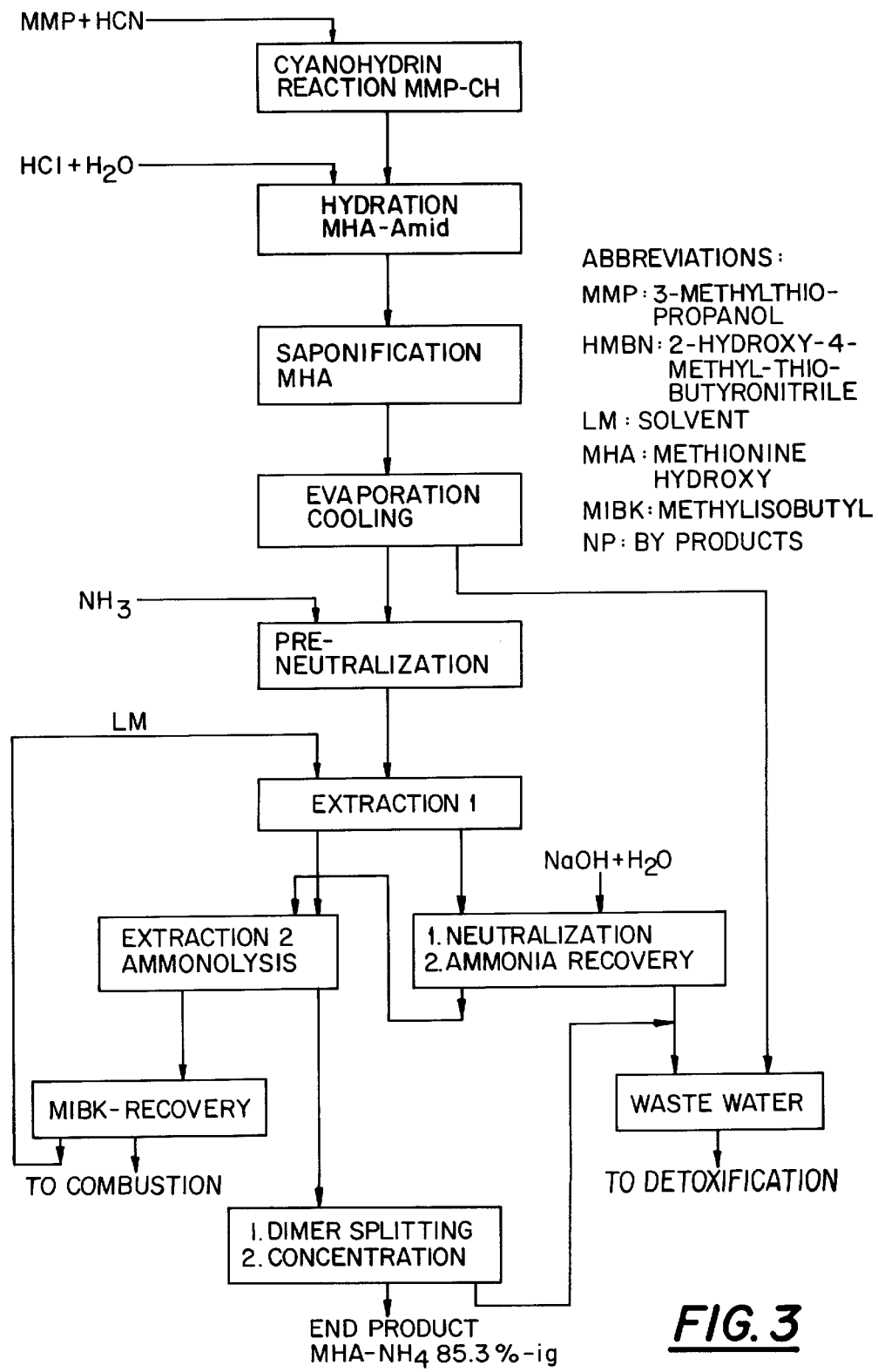
FIG. 3 shows a flow chart for the schematic course of the process of the invention.

The production of MHAAS described in example 11 is schematically shown in FIGS. 1 and 2 as a technical process with the main apparatuses and is explained in the following. As associated flow chart (FIG. 3) shows the schematic course again.

EXAMPLE 16

Preliminary remark:

The production of the cyanohydrin precursor from the educts MMP and HCN is included in the process description. Accordingly, the reaction part comprises a three-stage synthesis which can be carried out intermittently in batches as well as continuously whereas the following product workup takes place in every instance continuously. The process presented in the following refers to the flow chart with discontinuous conduction of the reaction shown in FIG. 1. In the case of a completely continuous operation a series of stirred-tank reactors or, as is shown in FIG. 2, a battery of 3 loop reactors with flow tubes connected at the outlet side replace the arrangement shown in FIG. 1 as reaction part.

I. Reaction

MMP is placed in a first reactor with external cooling circuit 1 and 100% HCN is charged in approximately 30 minutes in a slight excess of 3 molar % at temperatures around 30° C. while the pH is regulated constantly at 7.0 by the addition of triethylamine (TEA) and the reaction heat removed by rotating the mixture over the outer heat exchanger. After the end of the HCN infeed the mixture is allowed to react approximately another 30 minutes and the MMP-CH formed is transferred under cooling into an intermediate storage[1].

30–32% HCl is placed in a 14–10% molar excess in a second rector with external cooling circuit 2. The MMP-CH is charged within the shortest possible time under rotation cooling while the temperature is allowed to rise to 45° C. and is then held constant. The mixture is then allowed to react approximately another 30 minutes until the complete conversion of the cyanohydrin[2),3)]. The mixture is then discharged into jacketed reactor 3 heated with vapor and heated to 90-max 93° C. After a reaction time of 45 minutes the mixture is transferred for completion of the hydrolysis into jacketed and heated reactor 4 which functions both as secondary reactor as well as buffer container and in which the hydrolyzate is held for the subsequent continuous product workup.

II. Continuous product workup

The hydrolysis solution intermittently accumulated and dealcoholized in secondary reactor/buffer container 4 is supplied via a barometric dip to falling-film evaporator 5 standing under a vacuum and equipped with associated peripheral equipment. The product stream running off is cooled down thereby to approximately 60° C. as a consequence of adiabatic evaporation cooling while volatile impurities together with component amounts of water and hydrochloric acid are stripped off. The resulting vapors are quenched after partial cooling, at which time the majority of the excess HCl is condensed out as aqueous solution[4] and the remaining exhaust gas is conducted to an incinerator for combustion.

The dealcoholized hydrolysis solution passes under expansion into jacketed, coolable and heatable agitator container 6 provided with measuring and control devices for pH, temperature and level in which it is blunted with conc. ammonia solution at 40–50° C. to a pH of around +0.1.

The product stream running out of 6 is fed into the upper part of extraction column 7 provided with associated peripheral equipment while MIBK (or another suitable solvent) is conducted against it in countercurrent in an extraction agent/taker ratio of approximately 1.1–1.2. The resulting product current, which is now divided into two, is worked up further as follows:

The extract taken off at the top under cooling is drawn by suction via a buffer into sucking jet device 8 and mixed in it with approximately 20% ammonia solution recovered from the neutralization stage (see below) in a controlled excess of 1:1.1 to 1.3 moles. The neutralization of the MHA to MHAAS as well as the corresponding oligomer species to their ammonium salts takes place thereby along with their re-extraction into an aqueous phase. The mixture running off under cooling after the MHA/MHAAS conversion is taken up in a separator connected at the outlet side and belonging to 8 and processed further under separation of phases.

The organic upper phase is fed into distillation system 12 equipped with appropriate peripheral equipment. The MIBK purified by distillation and recovered therein is removed after passing a separator into solvent storage 16 from which it is recycled into the primary extraction circuit. The water remnants retained in the separator are returned via a collector into the distillation circuit. The removed bottom product is burned.

The aqueous lower phase, the eluate, is let off via a pre-heater into splitting/concentration system 9 consisting of two main apparatuses. The solution runs at first thereby through a residence-time column tempered to 90° C. and then passes into a distillation column operated under a slight vacuum and with reflux. The splitting of the oligomer portions takes place thereby as well as, at the same time, a concentration under removal of excess ammonia[5], which is combined as vapor product with the raffinate stream for the recovery of ammonia (see below). The concentrate running off out of the bottom under cooling and expansion runs through conditioning stretch 10 provided with mixing devices and with appropriate dosing and M+R devices in which stretch the desired product specification is adjusted by the selective addition of ammonia[5] and/or water. The conditioned end product is then taken into finished-product storage 11.

The raffinate running out of extraction column 7 and consisting essentially of a saturated to supersaturated ammonium chloride solution[6] is fed into distillation column 14 operated under a slight excess pressure while concentrated sodium hydroxide solution is mixed in under regulation of the pH via the associated heating circuit of the system. The ammonium salt is completely reacted thereby to sodium chloride and ammonia. The released ammonia is distilled out completely at the same time at ph'es>8 and transferred after the condensation as 20–25% aqueous solution into an $NH_3$ storage 15 and reserved there for the re-extraction and neutralization of the MHA under formation of MHAAS[6]. The bottom runoff, consisting essentially of a saturated solution of common salt, is put in a biological waste-water purification plant, if necessary under post-neutralization with hydrochloric acid[4] after analytic control[7].

Remarks:

[1]For the instance in which MMP-CH must be intermediately stored for a rather long time and/or uncooled, a safety stabilization, e.g. with phosphoric acid, equipped with appropriate auxiliary equipment, is to be provided. It is necessary for this that the storage contents are thoroughly mixed either by an agitator or by pump rotation (not shown in the scheme).

[2]The molar HCl excess is a function of the concentration of the acid and the higher the latter is the lower it is.

[3]A slight amount of MHA amide is already hydrolyzed further to MHA in the amidation stage.

[4]The recovered, aqueous HCl can be used as required for the neutralization of the waste water. Otherwise, it is recycled as process acid.

[5]During the splitting of oligomers a re-formation of MHA can occur to a certain extent as a function of the residence time and the temperature by hydrolysis under outgassing of $NH_3$. If the amount of MHA exceeds the desired specification limit of e.g. 5 to max. 10 molar % then the excess amount is post-neutralized in the conditioning stretch by the pH-controlled addition of $NH_3$. It is important in this case that no appreciable re-formation of oligomers occurs.

[6]The raffinate stream is contaminated as a function of the solvent selected—here with MIBK. The latter is then to be found in the dealcoholized and recondensed circuit ammonia. In order to prevent an accumulation, in which an unmixing takes place, the $NH_3$ condensation must be followed by a separator (not shown in the scheme).

[7]In particular, any residual cyanide content (from the vapor condensate of the evaporation cooling), in addition to the waste-water values such as BSB, TOC, is analytically monitored. If this cyanide content exceeds the allowable limit value it must be correspondingly lowered by mixing in hydrogen peroxide, e.g. into the heating circuit of 14.

EXAMPLE 17

Comparative nutritive tests

In comparative broiler growth tests the biological efficacy of the methionine analogues MHA and MHAAS was tested for 21 days on seven-day-old chicks. The weight increase and the feedstuff utilization of the seven-to-twenty-eight-day-old animals served as criteria. The starting point was an S-amino-acid-poor basal ration whose M+C content was raised from 0.40% to 0.68%. The methionine substitutes were placed in an equimolar manner thereby into the following 8 supplementation stages (in percentages):

0.02–0.04–0.07–0.10–0.14–0.18–0.23–0.28.

A. Composition of the basal ration

| Components % | Amino acids % | | | |
|---|---|---|---|---|
| 20.0 corn | M + C | 0.40 | Arg | 1.35 |
| 11.6 corn starch | Met | 0.19 | Ile | 0.80 |
| 29.93 tapioca | Cys | 0.21 | Val | 1.00 |
| 5.5 soy-bean oil | Lys | 1.15 | Leu | 1.35 |
| 5.5 cellulose | Thr | 0.80 | Trp | 0.22 |
| 20.0 soy-bean meal | | | | |
| 0.73 $CaCO_3$ | Na | | Ca | 0.95 |
| 2.2 $CaHPO_4 \times 2H_2O$ | | | P | 0.65 |

Energy (MJ/kg)
ME chicks 13.6

Figure 4A:
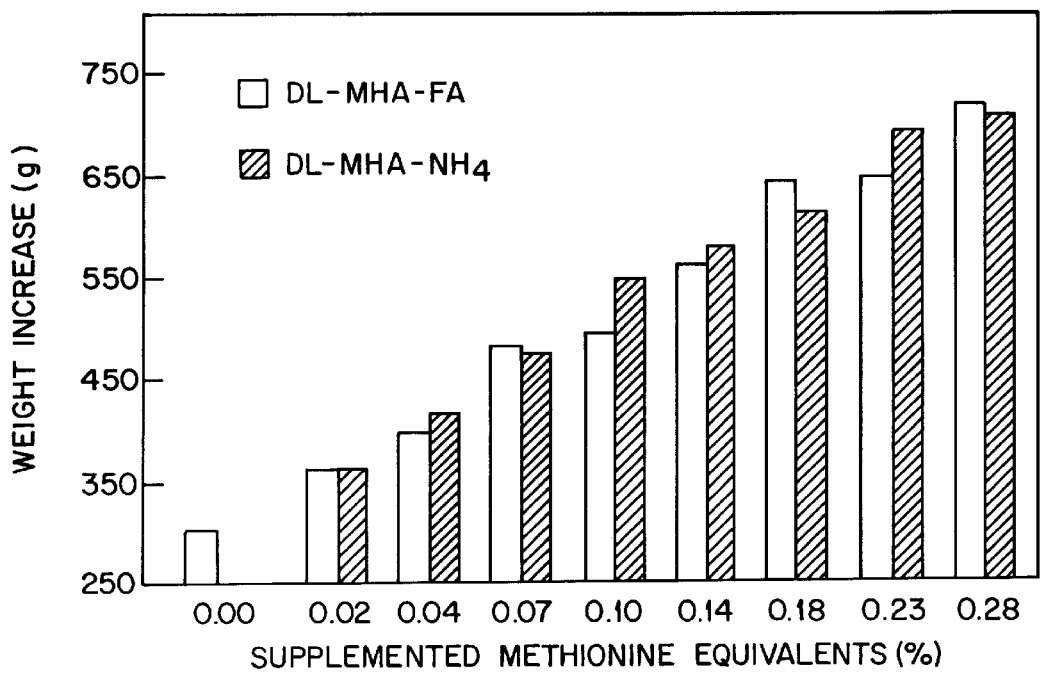
Figure 4B:
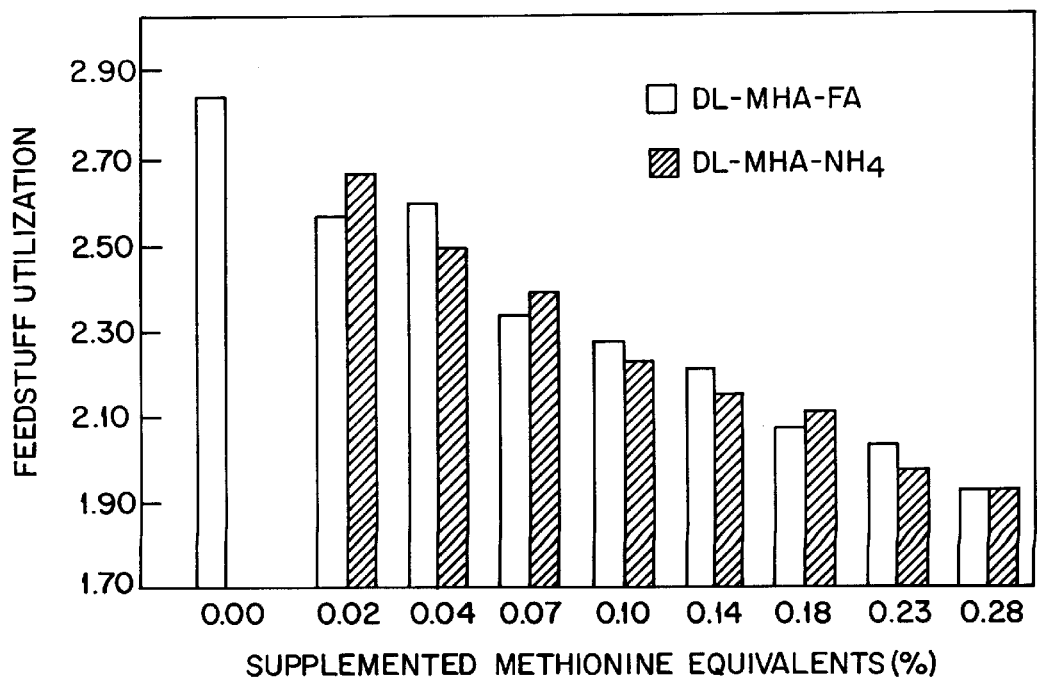
FIG. 4B bottom shows a recording of the feedstuff utilization of broilers compared to the supplemented methionine equivalents in (%) for various methionine sources for the same purpose as above.
Figure 5A:
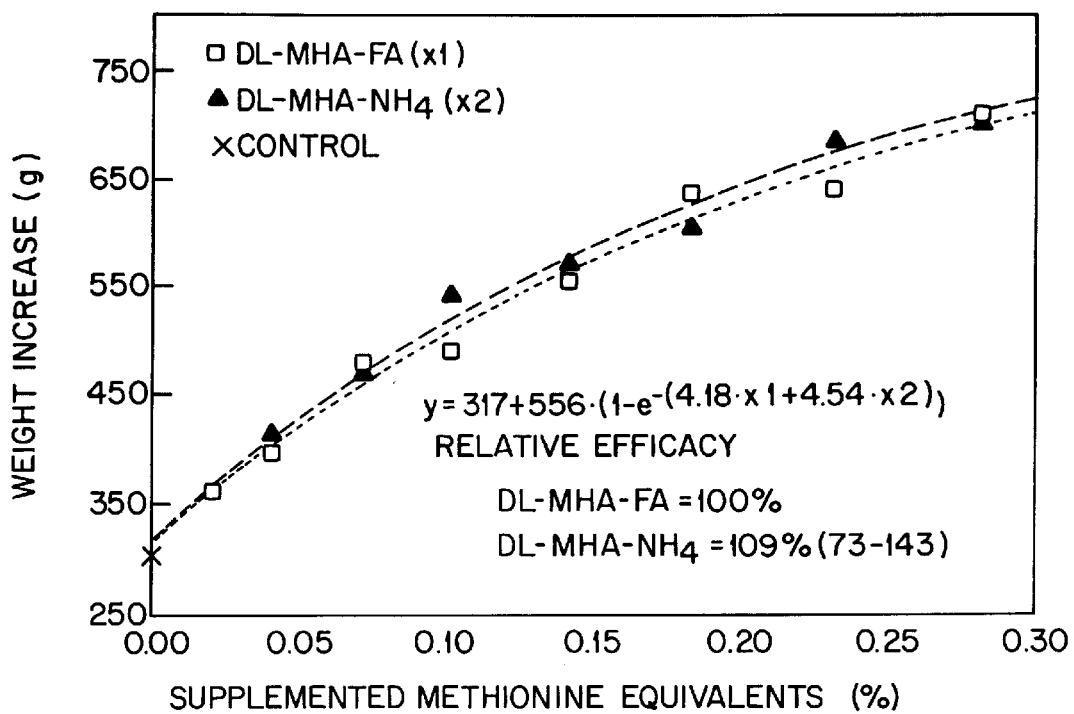
Figure 5B:
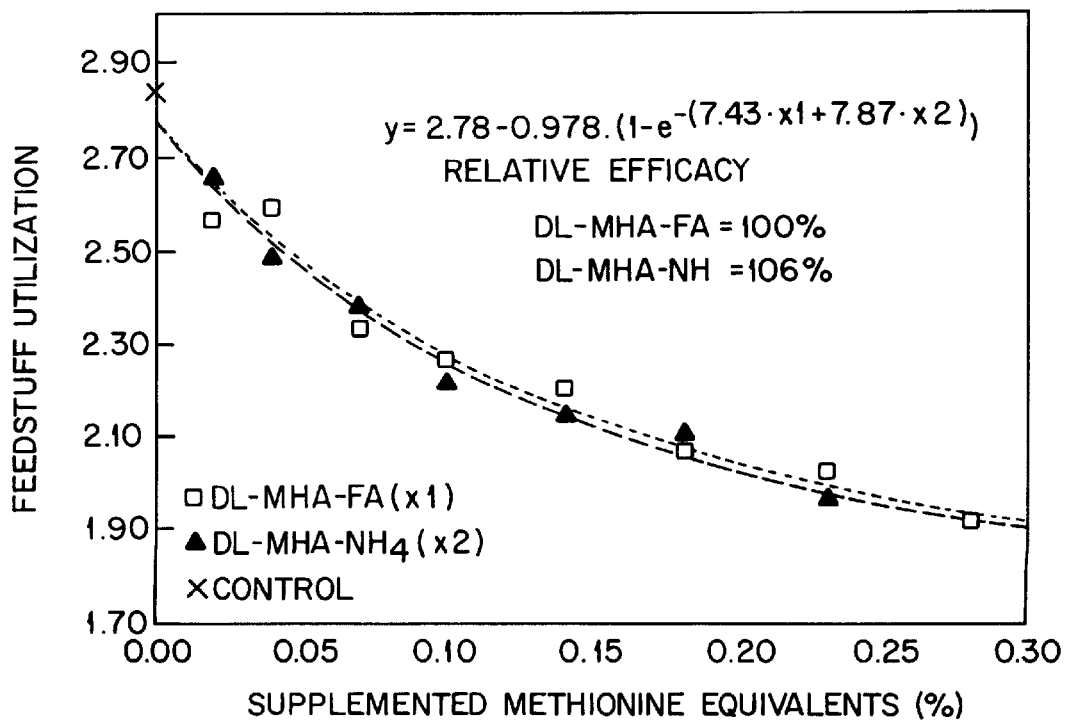
FIG. 5B bottom shows a graphic view of the feedstuff utilization of broilers compared to the supplemented methionine equivalents (%) for various methionine sources for the same purpose as above.

B. Test conditions
Seven-day-old broilers (chicks)
Number of animals: 1125
Repetitions: 3
Test time: 21 days C. Test results (see 2–4)
The achievements obtained in the individual treatment groups are apparent in table of results 1 and in the graphic presentations (FIGS. 4,5).

TABLE 1

Results: 7–28 days

| Group | Product | Dose | Weight Increase g | Feedstuff conversion | calculated feedstuff take-up g |
|---|---|---|---|---|---|
| 01 | control | 0.000 | 303 | 2.84 | 861 |
| 10 | DL-MHA (free acid) | 0.020 | 361 | 2.57 | 927 |
| 11 | DL-MHA (free acid) | 0.040 | 395 | 2.59 | 1024 |
| 12 | DL-MHA (free acid) | 0.070 | 478 | 2.33 | 1112 |
| 13 | DL-MHA (free acid) | 0.100 | 489 | 2.26 | 1105 |
| 14 | DL-MHA (free acid) | 0.140 | 554 | 2.19 | 1215 |
| 15 | DL-MHA (free acid) | 0.180 | 636 | 2.05 | 1306 |
| 16 | DL-MHA (free acid) | 0.230 | 640 | 2.01 | 1288 |
| 17 | DL-MHA (free acid) | 0.280 | 712 | 1.91 | 1360 |
| 18 | DL-MHA-$NH_4$ | 0.020 | 362 | 2.66 | 964 |
| 19 | DL-MHA-$NH_4$ | 0.040 | 413 | 2.49 | 1027 |
| 20 | DL-MHA-$NH_4$ | 0.070 | 469 | 2.38 | 1116 |
| 21 | DL-MHA-$NH_4$ | 0.100 | 542 | 2.21 | 1198 |
| 22 | DL-MHA-$NH_4$ | 0.140 | 572 | 2.13 | 1220 |
| 23 | DL-MHA-$NH_4$ | 0.180 | 605 | 2.09 | 1266 |
| 24 | DL-MHA-$NH_4$ | 0.230 | 685 | 1.96 | 1341 |
| 25 | DL-MHA-$NH_4$ | 0.280 | 703 | 1.91 | 1343 |

The achievements of the animals improved continuously both in weight increase and also in feedstuff utilization as the dosage of the methionine sources increased. A clear weight increase and an improvement of the feedstuff utilization was able to be achieved with the highest supplementation in comparison to the unsupplemented control group. On the whole, the test data shows a good response to the substances added. The average weight increase in the individual treatment groups in comparison to the unsupplemented control group was 230 g for MHA and 241 g for MHAAS. This yields a significance factor of 95.6% for MHA compared to MHAAS;

D. biological significance of the tho methionine analogues
An average significance of 93.3% relative to MHAAS was calculated for D,L MHA. Both methionine analogues are utilized distinctly more poorly than D,L methionine; however, MHAAS displayed a pronounced biological significance, namely about 6% higher.

Further details and advantages of the invention result from the following claims.

| Reference number list for figure 1 | |
|---|---|
| 1 | cyanohydrin reaction |
| 1a | to the wash |
| 1b | KW |
| 1c | MMP |
| 1d | HCN |
| 1e | TEA |
| 1f | KS |
| 1g | $H_3PO_4$ for safety stabilization |
| 1h | MMP-CN intermediate storage |
| 2 | amide reaction |
| 2a | KW |
| 2b | HCl 32% |
| 3 | saponification |
| 4 | post-reaction and buffer |
| 4a | to exhaust-air washer |
| 5 | evaporation cooling |
| 5a | falling-film evaporator |
| 5b | to incinerator |
| 5c | KW |
| 5d | waste water to biology |
| 6 | pre-neutralization |
| 6a | $NH_3$ from storage 15 |
| 7 | extraction I |
| 7a | MIBK from storage 14 |
| 7b | buffer |
| 7c | buffer |
| 8 | ammonolysis + extraction II |
| 8a | separator |
| 9 | dimer splitting |
| 10 | conditioning |
| 10a | fresh $NH_3$ |
| 10b | pH 7.0 |
| 11 | storage MHA-$NH_4$ 85% |
| 11a | to filling |
| 12 | MIBK distillation |
| 12a | removal to incinerator |
| 12b | KW |
| 12c | to collector 16 |
| 14 | MIBK storage |
| 14a | fresh MIBK |
| 14b | MIBK to extraction I |
| 14c | neutralization |
| 14d | NaOH 50% |
| 14e | fresh $NH_3$ |
| 15 | $NH_3$ storage 30% |
| 15a | waste water to biology |

What is claimed is:
1. A process for producing ammonium-2-hydroxy-4-methylthio-n-butyrate (MHAAS) comprising:
   a) isolating 2-hydroxy-4-methylthio-butyric acid (MHA), which MHA also contains dimers and higher oligomers, from a first reaction mixture wherein said first reaction mixture is obtained by attachment of hydrogen cyanide (HCN) to methylmercaptopropionaldehyde (MMP) followed by mineral-acidic hydrolysis of methylmercaptopropionaldehyde cyanohydrin (MMP-CH) so formed, with ammonia, to form a second reaction mixture,
   b) treating the second reaction mixture, resulting from step (a), with an inert solvent non-miscible or partially miscible with water to obtain a first organic extract and a first aqueous raffinate consisting essentially of ammonium chloride;
   c) decomposing the first organic extract by treatment with ammonia under phase separation conditions into a second organic extract and a second aqueous raffinate,
   d) reextracting the MHA as MHAAS into the second aqueous raffinate taking place with formation of salt, and e) isolating the MHAAS in an odorless free flowing solution from the second aqueous raffinate.

2. A process according to claim 1 wherein the first organic extract is treated with a sufficient amount of concentrated aqueous ammonia solution so that the MHA contained therein is neutralized to MHAAS.

3. A process according to claim 1 wherein the second aqueous raffinate is heated before and/or during the isolating of the MHAAS, optionally under reflux conditions.

4. A process according to claim 1 wherein the second aqueous raffinate is concentrated by evaporating off ammonia.

5. A process according to claims 3 or 4, wherein the second aqueous raffinate is heated under conditions that the dimeric and higher oligomeric portions of MHAAS as well as any residual MHA amide are split to the desired boundary limit under formation of further monomeric MHAAS.

6. A process according to claims 3 or 4 wherein the second aqueous raffinate is heated under conditions that a desired amount of MHA is re-formed by hydrolytically splitting the MHAAS with release of ammonia.

7. A process according to claim 1 wherein excess ammonia in the second aqueous raffinate is evaporated off for isolating the MHAAS in conjunction with a concentration by water evaporation by adiabatic evaporation cooling.

8. A process according to claim 1 wherein HCl is used for the mineral acidic hydrolysis of the MMP-CH.

9. A process according to claim 8 wherein hydrolysis of the MMP-CH is carried out in two stages and that in a first hydrolysis stage aqueous hydrochloric acid with a concentration of 15–40% by weight is used in a temperature range of 20–70° C. in a molar ratio of MMP-CH:HCl of 1:1.0 to 1:1.5.

10. A process according to claim 9 wherein HCl is added in such an amount and under such conditions that after the first hydrolysis stage MHA amide is produced from the MMP-CH and the reaction mixture produced thereby is free of cyanohydrin.

11. A process according to claims 9 or 10 wherein the reaction mixture obtained after the first hydrolysis stage is maintained in a second stage, optionally after dilution with water, at temperatures of 80–110° C. in order to complete the hydrolysis of MHA amide to MHA.

12. A process according to claim 1 wherein the reaction mixture obtained after the mineral hydrolysis is cooled to temperatures $\leq 70°$ C. by an adiabatic evaporation cooling in order to remove small amounts of volatile compounds.

13. A process according to claim 1 wherein the second reaction mixture is neutralized with a base after the hydrolysis and before the treatment with the solvent.

14. A process according to claim 13 wherein the second reaction mixture is adjusted with ammonia to a pH in a range of approximately −0.5 to +0.5.

15. A process according to claims 13 or 14 wherein the first aqueous raffinate, containing essentially of ammonium chloride, is treated with sodium hydroxide solution up to a pH $\geq 8$ with the release of ammonia and the formation of a sodium chloride solution saturated with ammonia.

16. A process according to claim 7 wherein the released ammonia is distilled off, and optionally concentrated and recycled for use in treating the second aqueous raffinate.

\* \* \* \* \*